United States Patent
Yang et al.

(10) Patent No.: US 11,117,859 B1
(45) Date of Patent: Sep. 14, 2021

(54) PLEUROMUTILIN HIPPURIC ACID ESTER WITH ANTIBACTERIAL ACTIVITY AND A METHOD OF PREPARING THE SAME

(71) Applicants: Dan Yang, Xi'an (CN); Jingyi Li, Xi'an (CN); Liang Xin, Xi'an (CN); Qianqian Zhao, Xi'an (CN); Liang Qi, Xi'an (CN); Bin Tian, Xi'an (CN); Jian Zha, Xi'an (CN); Wenbo Yao, Xi'an (CN); Gennian Mao, Xi'an (CN); Han Li, Xi'an (CN); Chunyang Shi, Xi'an (CN); Yongbo Wang, Xi'an (CN); Jingwen Xu, Xi'an (CN)

(72) Inventors: Dan Yang, Xi'an (CN); Jingyi Li, Xi'an (CN); Liang Xin, Xi'an (CN); Qianqian Zhao, Xi'an (CN); Liang Qi, Xi'an (CN); Bin Tian, Xi'an (CN); Jian Zha, Xi'an (CN); Wenbo Yao, Xi'an (CN); Gennian Mao, Xi'an (CN); Han Li, Xi'an (CN); Chunyang Shi, Xi'an (CN); Yongbo Wang, Xi'an (CN); Jingwen Xu, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 17/175,575

(22) Filed: Feb. 12, 2021

(51) Int. Cl.
*C07C 231/24* (2006.01)
*C07C 233/83* (2006.01)
*C07C 231/12* (2006.01)

(52) U.S. Cl.
CPC .......... *C07C 233/83* (2013.01); *C07C 231/12* (2013.01); *C07C 231/24* (2013.01); *C07B 2200/13* (2013.01)

(58) Field of Classification Search
CPC ... C07C 233/83; C07C 231/24; C07C 231/12; C07B 2200/13
See application file for complete search history.

(56) References Cited

PUBLICATIONS

Shang et al. (Chemical Synthesis and Biological Activities of Novel Pleuromutilin Derivatives with Substituted Amino Moiety, PLOS One, vol. 8, issue 12, pp. 1-10, Published 2013) (Year: 2013).*
ChemSpider (1 page, Published 2008) (Year: 2008).*

* cited by examiner

*Primary Examiner* — Yevgeny Valenrod
*Assistant Examiner* — Blaine G Doletski

(57) ABSTRACT

A compound with anti-drug resistant bacteria activity having the following formula

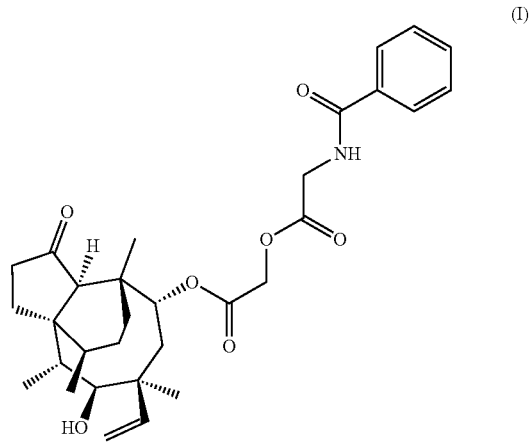

(I) is disclosed. The methods of preparing the compound of formula (I) are also disclosed.

16 Claims, 2 Drawing Sheets

PLEUROMUTILIN HIPPURIC ACID ESTER WITH ANTIBACTERIAL ACTIVITY AND A METHOD OF PREPARING THE SAME

FIELD OF THE INVENTION

The present invention relates to the field of medicinal chemistry, and in particular, to a pleuromutilin hippuric acid ester with antibacterial activity and a method of preparing the same.

BACKGROUND OF THE INVENTION

In recent years, various types of drug-resistant bacteria have developed rapidly, making the drug resistance rate and infectious problems more serious. Bacterial resistance has become a serious public health challenge facing the world, and the widespread use of antibacterial drugs is the main reason for the large number of resistant bacteria. The infection rate of multidrug-resistant bacteria (MDROs) and the mortality of patients have been increasing year by year. Bacterial drug resistance is becoming more and more serious. It is particularly important to find compounds with good antibacterial activity, unique antibacterial mechanism and new structures.

Hippuric acid (compound formula III) is naturally present in the urine of herbivores (such as horses), and there is also a small amount in human urine. Hippuric acid is easily hydrolyzed into benzoic acid and glycine. Hippuric acid can lower the pH value of urine within a certain range, change the living environment of bacteria, and play a synergistic bactericidal effect.

Pleuromutilin (compound of formula II) is a tricyclic diterpenoid veterinary antibiotic produced by submerged fermentation of *Clitopilus pinsitus*. It has antibacterial activity against Gram-positive bacteria and *Mycoplasma*. The main structure for its antibacterial effect is the tricyclic skeleton in the compound, which can form an inducing fit effect with the peptide acyltransferase active center (PTC) of the 50S subunit of the bacterial ribosome.

In the present invention, pleuromulin is combined with hippuric acid to obtain a pleuromutilin hippuric acid ester. Preliminary in vitro antibacterial activity experiment shows that the compound has excellent antibacterial activity and anti-drug-resistant bacteria activity.

SUMMARY OF THE INVENTION

In one embodiment, the present invention provides a compound having the following formula (I) (pleuromutilin hippuric acid ester):

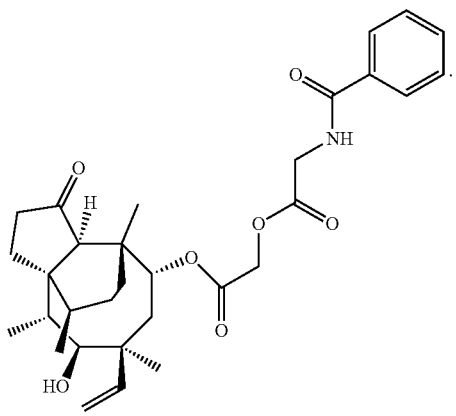

(I)

In another embodiment, a method of preparing the compound of formula (I) includes: reacting a compound of formula (II) with a compound of formula (III) to obtain the compound of formula (I):

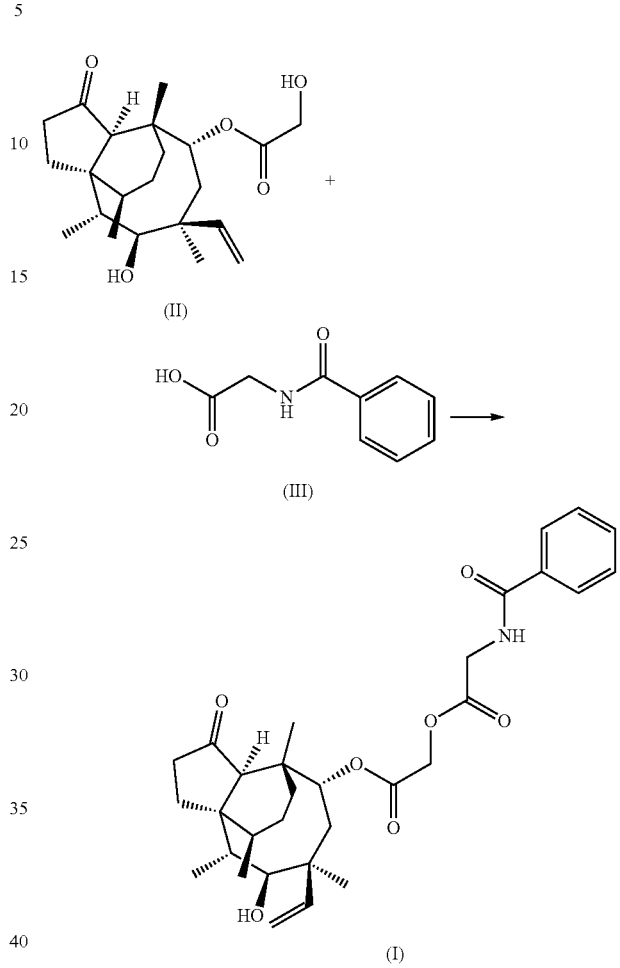

In another embodiment, the reaction of the compound of formula (II) with the compound of formula (III) includes the following steps: placing the compound of formula (II) and the compound of formula (III), in a molar ratio of 1:1 to 1:1.3, in a reactor; adding an organic solvent and a catalytic amount of 4-dimethylaminopyridine (4-DMAP) under nitrogen atmosphere to obtain a reaction mixture; stirring the reaction mixture at 0° C. for five minutes and then adding N,N'-dicyclohexylcarbodiimide (DCC) to the reaction mixture; reacting the reaction mixture at 25-70° C. for 3 to 7 hours; concentrating the reaction mixture and extracting with ethyl acetate to obtain a crude product; and purifying the crude product on a silica gel fresh chromatography column with petroleum ether and ethyl acetate with a ratio of 1:1 to 4:1 as an eluent to obtain the compound of formula (I).

In another embodiment, the organic solvent is toluene, 1,2-dichloroethane, or dimethylformamide (DMF).

In another embodiment, the organic solvent is 1,2-dichloroethane.

In another embodiment, the molar ratio of the compound of formula (II) and the compound of formula (III) is 1:1.1.

In another embodiment, the reaction mixture is heated at 60° C.

In another embodiment, the reaction mixture is reacted for 5 hours.

In another embodiment, the eluent is petroleum ether: ethyl acetate=3:1.

In another embodiment, the reaction of the compound of formula (II) with the compound of formula (III) includes the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (III) to the reactor to form a reaction mixture; heating the reaction mixture at 20-60° C. for 4-8 hours; placing the reaction mixture in a separating funnel to separate a crude product; purifying the crude product by recrystallization in methanol to obtain the compound of formula (I); and recycling the ionic liquid.

In another embodiment, the ionic liquid is 1-octyl-3-methylimidazolium hexafluorophosphate ($C_{12}H_{23}F_6N_2P$),1-hexyl-3-methylimidazolium tetrafluoroborate or 1-butyl-3-methylimidazolium tetrafluoroborate.

In another embodiment, the ionic liquid is the ionic liquid is 1-octyl-3-methylimidazolium hexafluorophosphate.

In another embodiment, the compound of formula (II) and the compound (III) have a molar ratio of 1:1 to 1:1.3.

In another embodiment, the molar ratio of the compound of formula (II) and the compound of formula (III) is 1:1.1.

In another embodiment, the reaction mixture is heated at 30° C.

In another embodiment, the reaction mixture is heated for 6 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
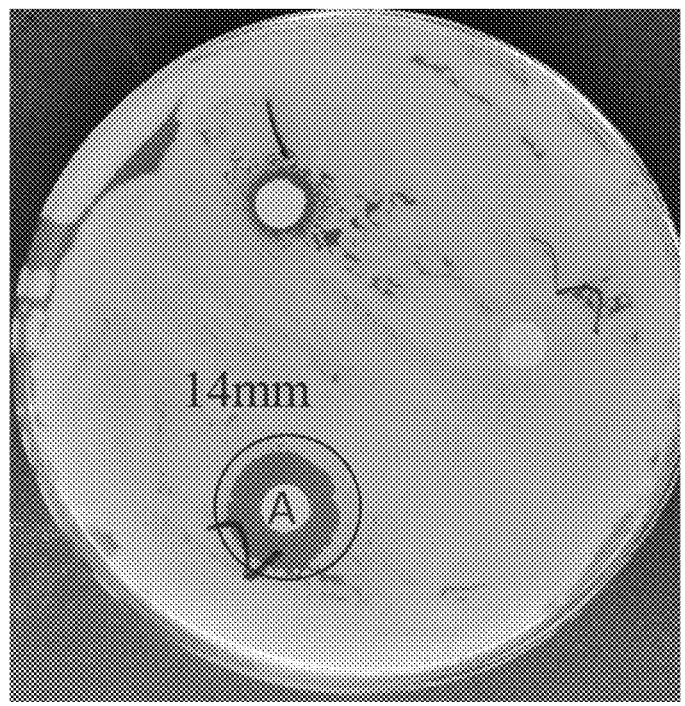
FIG. 1 shows the in vitro antibacterial activity of the pleuromutilin hippuric acid ester against drug-resistant bacteria MRSA 171.

Reference will now be made in detail to embodiments of the present invention, example of which is illustrated in the accompanying drawings. The following examples illustrate the present invention, but the present invention is not limited to the following examples.

Example 1

Preparation of Compound of Formula (I) (3aS,4R,5S,6S,8R,9R,9aR,12R)-5-hydroxy-4,6,9,12-tetramethyl-1-oxo-6-vinyldecahydro-3a,9-propanocyclopenta[8]annulen-8-yl 2-(2-benzamidoacetoxy)acetate)

In a 100 mL three-necked flask, 378.5 mg (1.00 mmol) of pleuromutilin and 3.7 mg (0.03 mmol) 4-DMAP were dissolved in 20 mL of 1,2-dichloroethane under nitrogen atmosphere. 197.1 mg (1.10 mmol) of hippuric acid was dissolved in 15 mL of 1,2-dichloroethane, and added dropwise to the reaction mixture by a separatory funnel. After the completion of the dropwise addition, the reaction mixture was stirred at 0° C. for 5 minutes, and 206.3 mg (1.00 mmol) of coupling agent DCC was added. The ice bath was removed, and the reaction was heated at 60° C. for 5 hours. Thin layer chromatography was used to track the reaction to completion. The reaction mixture was concentrated, washed with water, and extracted with ethyl acetate. Ethyl acetate was dried and concentrated to obtain a crude product. The crude product was purified by silica gel column chromatography, with petroleum ether:ethyl acetate=3:1 as eluent, and the eluent was concentrated under reduced pressure and dried to obtain 391.4 mg of the titled compound, a yield of 72.53%.

$^1$H-NMR (400 MHz, chloroform-d) δ (ppm): 7.86 (2H, d), 7.58 (1H, d), 7.50 (2H, d), 6.73 (1H, s), 6.52 (1H, m), 5.85 (1H, d), 5.41 (1H, d), 5.28 (1H, d), 4.73 (2H, m), 4.42 (2H, d), 3.52 (1H, s), 3.41 (1H, d), 2.38 (1H, s), 2.25 (4H, m), 1.80-1.36 (11H, m), 1.22 (3H, s), 0.94 (3H, d), 0.81 (3H, d); $^{13}$C-NMR (400 MHz, chloroform-d) δ ppm): 216.7, 169.5, 167.4, 166.1, 138.7, 131.9, 128.6, 127.1, 117.4, 74.6, 70.1, 58.0, 50.8, 45.4, 44.6, 44.0, 41.8, 36.6, 36.1, 34.4, 30.4, 26.8, 26.4, 24.8, 16.5, 14.7, 11.4.

Example 2

Preparation of Compound of Formula (I)

In a 100 mL three-necked flask, 378.5 mg (1.00 mmol) of pleuromutilin and 3.7 mg (0.03 mmol) 4-DMAP were dissolved in 20 mL of 1,2-dichloroethane under nitrogen atmosphere. 197.1 mg (1.10 mmol) of hippuric acid was dissolved in 15 mL of 1,2-dichloroethane, and added dropwise to the reaction mixture by a separatory funnel. After the completion of the dropwise addition, the reaction mixture was stirred at 0° C. for 5 minutes, and 206.3 mg (1.00 mmol) of coupling agent DCC was added. The ice bath was removed, and the reaction was heated at 40° C. for 3 hours. Thin layer chromatography was used to track the reaction to completion. The reaction mixture was concentrated, washed with water, and extracted with ethyl acetate. Ethyl acetate was dried and concentrated to obtain a crude product. The crude product was purified by silica gel column chromatography, with petroleum ether:ethyl acetate=3:1 as eluent, and the eluent was concentrated under reduced pressure and dried to obtain 380.4 mg of the titled compound, a yield of 70.49%.

Example 3

Preparation of Compound of Formula (I)

In a 100 mL three-necked flask, 378.5 mg (1.00 mmol) of pleuromutilin and 3.7 mg (0.03 mmol) 4-DMAP were dissolved in 20 mL of 1,2-dichloroethane under nitrogen atmosphere. 215.0 mg (1.20 mmol) of hippuric acid was dissolved in 15 mL of 1,2-dichloroethane, and added dropwise to the reaction mixture by a separatory funnel. After the completion of the dropwise addition, the reaction mixture was stirred at 0° C. for 5 minutes, and 206.3 mg (1.00 mmol) of coupling agent DCC was added. The ice bath was removed, and the reaction was heated at 50° C. for 5 hours. Thin layer chromatography was used to track the reaction to completion. The reaction mixture was concentrated, washed with water, and extracted with ethyl acetate. Ethyl acetate was dried and concentrated to obtain a crude product. The crude product was purified by silica gel column chromatography, with petroleum ether:ethyl acetate=3:1 as eluent, and the eluent was concentrated under reduced pressure and dried to obtain 369.5 mg of the titled compound, a yield of 68.47%.

Example 4

Preparation of Compound of Formula (I)

In a 100 mL three-necked flask, 378.5 mg (1.00 mmol) of pleuromutilin and 3.7 mg (0.03 mmol) 4-DMAP were dissolved in 20 mL of DMF under nitrogen atmosphere. 232.9 mg (1.30 mmol) of hippuric acid was dissolved in 15 mL of DMF, and added dropwise to the reaction mixture by a separatory funnel. After the completion of the dropwise addition, the reaction mixture was stirred at 0° C. for 5 minutes, and 206.3 mg (1.00 mmol) of coupling agent DCC was added. The ice bath was removed, and the reaction was heated at 30° C. for 5 hours. Thin layer chromatography was used to track the reaction to completion. The reaction mixture was concentrated, washed with water, and extracted with ethyl acetate. Ethyl acetate was dried and concentrated to obtain a crude product. The crude product was purified by silica gel column chromatography, with petroleum ether:ethyl acetate=2:1 as eluent, and the eluent was concentrated under reduced pressure and dried to obtain 321.7 mg of the titled compound, a yield of 59.61%.

Example 5

Preparation of Compound of Formula (I)

In a 100 mL three-necked flask, 378.5 mg (1.00 mmol) of pleuromutilin and 3.7 mg (0.03 mmol) 4-DMAP were dissolved in 20 mL of DMF under nitrogen atmosphere. 232.9 mg (1.30 mmol) of hippuric acid was dissolved in 15 mL of DMF, and added dropwise to the reaction mixture by a separatory funnel. After the completion of the dropwise addition, the reaction mixture was stirred at 0° C. for 5 minutes, and 206.3 mg (1.00 mmol) of coupling agent DCC was added. The ice bath was removed, and the reaction was heated at 25° C. for 5 hours. Thin layer chromatography was used to track the reaction to completion. The reaction mixture was concentrated, washed with water, and extracted with ethyl acetate. Ethyl acetate was dried and concentrated to obtain a crude product. The crude product was purified by silica gel column chromatography, with petroleum ether:ethyl acetate=3:1 as eluent, and the eluent was concentrated under reduced pressure and dried to obtain 313.6 mg of the titled compound, a yield of 58.11%.

Example 6

Preparation of Compound of Formula (I)

In a 100 mL three-necked flask, 378.5 mg (1.00 mmol) of pleuromutilin and 3.7 mg (0.03 mmol) 4-DMAP were dissolved in 20 mL of toluene under nitrogen atmosphere. 232.9 mg (1.30 mmol) of hippuric acid was dissolved in 15 mL of toluene, and added dropwise to the reaction mixture by a separatory funnel. After the completion of the dropwise addition, the reaction mixture was stirred at 0° C. for 5 minutes, and 206.3 mg (1.00 mmol) of coupling agent DCC was added. The ice bath was removed, and the reaction was heated at 60° C. for 3 hours. Thin layer chromatography was used to track the reaction to completion. The reaction mixture was concentrated, washed with water, and extracted with ethyl acetate. Ethyl acetate was dried and concentrated to obtain a crude product. The crude product was purified by silica gel column chromatography, with petroleum ether:ethyl acetate=3:1 as eluent, and the eluent was concentrated under reduced pressure and dried to obtain 338.5 mg of the titled compound, a yield of 62.73%.

Example 7

Preparation of Compound of Formula (I)

In a 100 mL three-necked flask, 378.5 mg (1.00 mmol) of pleuromutilin and 3.7 mg (0.03 mmol) 4-DMAP were dissolved in 20 mL of toluene under nitrogen atmosphere. 220.4 mg (1.10 mmol) of hippuric acid was dissolved in 15 mL of toluene, and added dropwise to the reaction mixture by a separatory funnel. After the completion of the dropwise addition, the reaction mixture was stirred at 0° C. for 5 minutes, and 206.3 mg (1.00 mmol) of coupling agent DCC was added. The ice bath was removed, and the reaction was heated at 70° C. for 6 hours. Thin layer chromatography was used to track the reaction to completion. The reaction mixture was concentrated, washed with water, and extracted with ethyl acetate. Ethyl acetate was dried and concentrated to obtain a crude product. The crude product was purified by silica gel column chromatography, with petroleum ether:ethyl acetate=4:1 as eluent, and the eluent was concentrated under reduced pressure and dried to obtain 369.3 mg of the titled compound, a yield of 67.32%.

Example 8

Preparation of Compound of Formula (I)

In a 100 mL three-necked flask, 378.5 mg (1.00 mmol) of pleuromutilin and 3.7 mg (0.03 mmol) 4-DMAP were dissolved in 20 mL of toluene under nitrogen atmosphere. 215.0 mg (1.20 mmol) of hippuric acid was dissolved in 15 mL of toluene, and added dropwise to the reaction mixture by a separatory funnel. After the completion of the dropwise addition, the reaction mixture was stirred at 0° C. for 5 minutes, and 206.3 mg (1.00 mmol) of coupling agent DCC was added. The ice bath was removed, and the reaction was heated at 50° C. for 4 hours. Thin layer chromatography was used to track the reaction to completion. The reaction mixture was concentrated, washed with water, and extracted with ethyl acetate. Ethyl acetate was dried and concentrated to obtain a crude product. The crude product was purified by silica gel column chromatography, with petroleum ether:ethyl acetate=2:1 as eluent, and the eluent was concentrated under reduced pressure and dried to obtain 329.8 mg of the titled compound, a yield of 61.11%.

Example 9

Preparation of Compound of Formula (I)

In a 100 mL three-necked flask, 378.5 mg (1.00 mmol) of pleuromutilin and 3.7 mg (0.03 mmol) 4-DMAP were dissolved in 20 mL of DMF under nitrogen atmosphere. 179.17 mg (1.00 mmol) of hippuric acid was dissolved in 15 mL of DMF, and added dropwise to the reaction mixture by a separatory funnel. After the completion of the dropwise addition, the reaction mixture was stirred at 0° C. for 5 minutes, and 206.3 mg (1.00 mmol) of coupling agent DCC was added. The ice bath was removed, and the reaction was heated at 70° C. for 7 hours. Thin layer chromatography was used to track the reaction to completion. The reaction mixture was concentrated, washed with water, and extracted with ethyl acetate. Ethyl acetate was dried and concentrated to obtain a crude product. The crude product was purified by silica gel column chromatography, with petroleum ether: ethyl acetate=3:1 as eluent, and the eluent was concentrated under reduced pressure and dried to obtain 359.3 mg of the titled compound, a yield of 66.58%.

Example 10

Preparation of Compound of Formula (I)

In a 100 mL three-necked flask, 378.5 mg (1.00 mmol) of pleuromutilin and 3.7 mg (0.03 mmol) 4-DMAP were dissolved in 20 mL of DMF under nitrogen atmosphere. 232.9 mg (1.30 mmol) of hippuric acid was dissolved in 15 mL of DMF, and added dropwise to the reaction mixture by a separatory funnel. After the completion of the dropwise addition, the reaction mixture was stirred at 0° C. for 5 minutes, and 206.3 mg (1.00 mmol) of coupling agent DCC was added. The ice bath was removed, and the reaction was heated at 60° C. for 3 hours. Thin layer chromatography was used to track the reaction to completion. The reaction mixture was concentrated, washed with water, and extracted with ethyl acetate. Ethyl acetate was dried and concentrated to obtain a crude product. The crude product was purified by silica gel column chromatography, with petroleum ether: ethyl acetate=4:1 as eluent, and the eluent was concentrated under reduced pressure and dried to obtain 351.2 mg of the titled compound, a yield of 65.08%.

Example 11

Preparation of Compound of Formula (I)

In a 100 mL three-necked flask, 378.5 mg (1.00 mmol) of pleuromutilin and 3.7 mg (0.03 mmol) 4-DMAP were dissolved in 20 mL of 1,2-dichloroethane under nitrogen atmosphere. 197.1 mg (1.10 mmol) of hippuric acid was dissolved in 15 mL of 1,2-dichloroethane, and added dropwise to the reaction mixture by a separatory funnel. After the completion of the dropwise addition, the reaction mixture was stirred at 0° C. for 5 minutes, and 206.3 mg (1.00 mmol) of coupling agent DCC was added. The ice bath was removed, and the reaction was heated at 30° C. for 5 hours. Thin layer chromatography was used to track the reaction to completion. The reaction mixture was concentrated, washed with water, and extracted with ethyl acetate. Ethyl acetate was dried and concentrated to obtain a crude product. The crude product was purified by silica gel column chromatography, with petroleum ether:ethyl acetate=1:1 as eluent, and the eluent was concentrated under reduced pressure and dried to obtain 335.0 mg of the titled compound, a yield of 62.07%.

Example 12

Preparation of Compound of Formula (I)

In a 250 mL three-necked flask, 378.5 mg (1.00 mmol) of pleuromutilin, 197.1 mg (1.10 mmol) of hippuric acid and 20.3 mg (0.011 mmol) silicomolybdic acid were dissolved in 100 mL of 1-octyl-3-methylimidazolium hexafluorophosphate under nitrogen atmosphere. After full dissolution, the reaction mixture was heated 30° C. for 6 hours. Thin layer chromatography was used to track the reaction to completion, heating was stopped, and the protective device was removed. The reaction mixture system was allowed to separate into layers to give a crude product. The crude product was recrystallized with 50 mL methanol to was 461.0 mg of the titled compound, a yield of 85.43%. 1-Octyl-3-methylimidazolium hexafluorophosphate was recovered.

Example 13

Preparation of Compound of Formula (I)

In a 250 mL three-necked flask, 378.5 mg (1.00 mmol) of pleuromutilin, 197.1 mg (1.10 mmol) of hippuric acid and 20.3 mg (0.011 mmol) silicomolybdic acid were dissolved in 100 mL of 1-butyl-3-methylimidazolium tetrafluoroborate under nitrogen atmosphere. After full dissolution, the reaction mixture was heated 40° C. for 5 hours. Thin layer chromatography was used to track the reaction to completion, heating was stopped, and the protective device was removed. The reaction mixture system was allowed to separate into layers to give a crude product. The crude product was recrystallized with 50 mL methanol to was 445.6 mg of the titled compound, a yield of 82.57%. 1-Butyl-3-methylimidazolium tetrafluoroborate was recovered.

Example 14

Preparation of Compound of Formula (I)

In a 250 mL three-necked flask, 378.5 mg (1.00 mmol) of pleuromutilin, 197.1 mg (1.10 mmol) of hippuric acid and 20.3 mg (0.011 mmol) silicomolybdic acid were dissolved in 100 mL of 1-hexyl-3-methylimidazolium tetrafluoroborate under nitrogen atmosphere. After full dissolution, the reaction mixture was heated 60° C. for 4 hours. Thin layer chromatography was used to track the reaction to completion, heating was stopped, and the protective device was removed. The reaction mixture system was allowed to separate into layers to give a crude product. The crude product was recrystallized with 50 mL methanol to was 451.6 mg of the titled compound, a yield of 83.68%. 1-Hexyl-3-methylimidazolium tetrafluoroborate was recovered.

Example 15

Preparation of Compound of Formula (I)

In a 250 mL three-necked flask, 378.5 mg (1.00 mmol) of pleuromutilin, 197.1 mg (1.10 mmol) of hippuric acid and 20.3 mg (0.011 mmol) silicomolybdic acid were dissolved in 100 mL of 1-octyl-3-methylimidazolium hexafluorophosphate under nitrogen atmosphere. After full dissolution, the reaction mixture was heated 35° C. for 4 hours. Thin layer chromatography was used to track the reaction to completion, heating was stopped, and the protective device was removed. The reaction mixture system was allowed to separate into layers to give a crude product. The crude product was recrystallized with 50 mL methanol to was 441.1 mg of the titled compound, a yield of 81.73%. 1-Octyl-3-methylimidazolium hexafluorophosphate was recovered.

Example 16

Antibacterial Activity Test of the Compounds of the Invention

The antimicrobial efficacy was determined by a paper diffusion method drug sensitivity test.

Experimental strains: multi-resistant *Staphylococcus aureus* 171, multi-resistant *Staphylococcus aureus* 575, multi-resistant *Staphylococcus aureus* 596. The experimental strain was identified by Huashan Hospital, Fudan University (Institute of Antibiotic of Fudan University).

Drug sensitive paper: The drug sensitive paper was a special drug sensitive paper with a diameter of 6.35 mm and a water absorption of 0.02 mL. The control drug was vancomycin (30 μg/tablet); the test drugs were pleuromutilin (30 μg/tablet), hippuric acid (30 μg/tablet) and pleuromutilin hippuric acid ester (30 μg/tablet).

Reagents: LB agar medium, LA broth medium, 0.5% DMSO solution.

Equipment: Ultra-clean workbench, high-pressure sterilization pot, gas bath constant temperature shaking incubator.

Preparation of Bacterial Suspension:

The experimental strains were inoculated in non-selective medium and placed in air at 37° C. for 24 h. A single colony that grows well and inoculate it into broth medium was incubate at 35° C.±2° C. for 6 hours, and LA broth medium was used to calibrate the concentration of the bacterial solution to 0.5 Mie turbidimetric tube ($1.5 \times 10^8$ CFU/mL). A bacterial suspension was obtained.

Paper Diffusion Method Drug Sensitivity Test:

LB dry powder was weighed, sterilized at 103.4 Kpa, 121.3° C. high-pressure steam for 15 min, and then placed it in a 40° C.-50° C. water bath. A sterile empty plate (inner diameter 9 cm) was placed on the surface of the ultra-clean table water table, and LB dry powder was poured to the plate. The thickness of each plate was 3 mm to 4 mm. After the plate was cooled at room temperature, it was stored in the refrigerator at 2° C.-8° C. A sterile cotton swab was used to dip the bacterial solution and ti evenly coat the surface of the LB plate 3 times. After inoculation of the bacterial suspension, the LB plate was dried at room temperature for 3 min to 5 min. Sterile forceps were used to closely attach the antibacterial drug paper to the dish. The dish was put upside down and placed in a 37° C. incubator for 24 h. The results were observed by measuring the diameter. Taking 0.5% DMSO solution as a negative control, the antibacterial activity is expressed by the diameter of the inhibition zone. The inhibition zone ≥17 mm, sensitive; the inhibition zone of 15 mm-16 mm, intermediary; the inhibition zone ≤14 mm, drug resistance.

Figure 2:
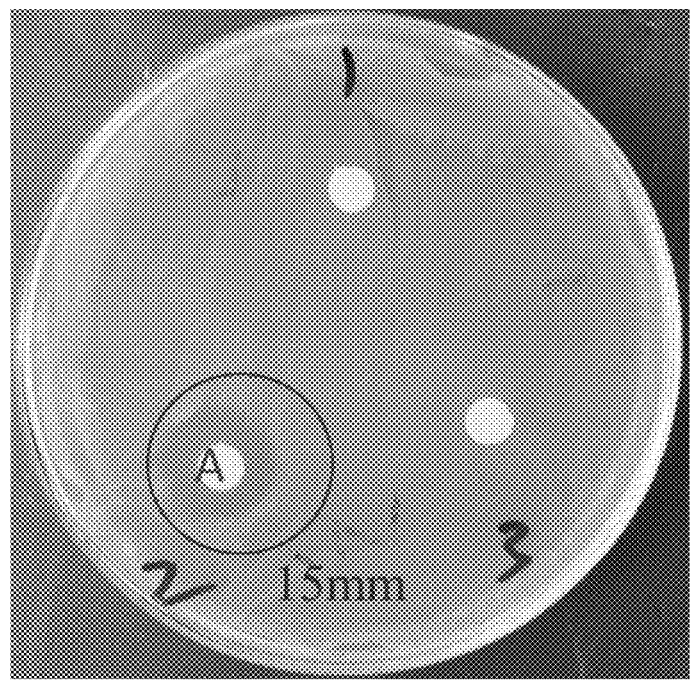
FIG. 2 shows the in vitro antibacterial activity of pleuromutilin hippuric acid ester against drug-resistant bacteria MRSA 575.
Figure 3:
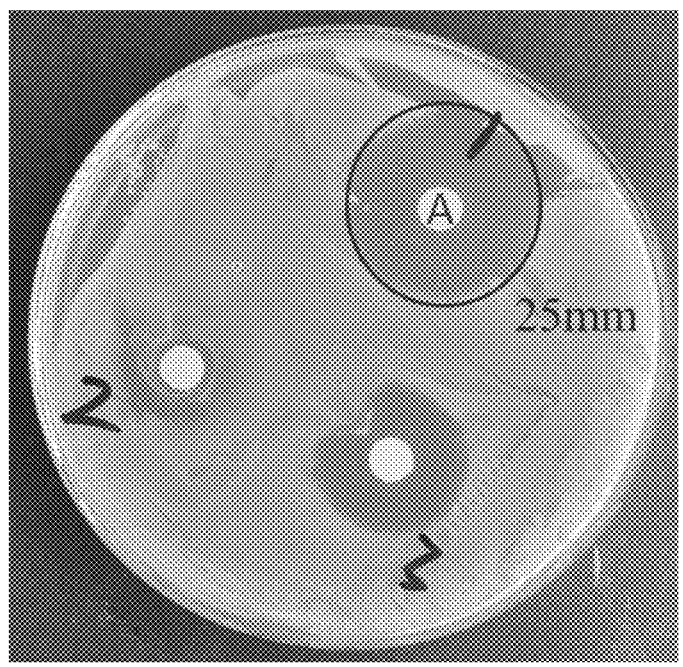
FIG. 3 shows the in vitro antibacterial activity of the pleuromutilin hippuric acid ester against drug-resistant bacteria MRSA 596.

In FIGS. 1-3, pleuromutilin hippuric acid ester is represented by the letter A. FIG. 1 shows the antibacterial effect of pleuromutilin hippuric acid ester on MRSA-171. FIG. 2 shows the antibacterial effect of pleuromutilin hippuric acid ester on *Salmonella*. FIG. 3 shows the antibacterial effect of pleuromutilin hippuric acid ester on *Escherichia coli*. The results are shown in Table 1.

TABLE 1

Experimental results of the zone of inhibition

| Compound | Zone of Inhibition/mm Strain | | |
|---|---|---|---|
| | MRSA-171 | MRSA-575 | MRSA-596 |
| 0.5% DMSO | 0 | 0 | 0 |
| Vancomycin | 15 | 17 | 23 |
| Pleuromutilin | 0 | 0 | 0 |
| Hippuric acid | 0 | 0 | 0 |
| Pleuromutilin hippuric acid ester | 14 | 15 | 25 |

The results in FIGS. 1-3 and Table 1 show that pleuromutilin and hippuric acid have no inhibitory effect on drug-resistant bacteria. The pleuromutilin hippuric acid ester has strong inhibitory effects on multi-drug resistant *Staphylococcus aureus* 171, 575, 596, and the diameter of bacteriostatic zone against multidrug resistant *Staphylococcus aureus* 596 was up to 25 mm. In summary, the pleuromutilin hippuric acid ester of the present invention can be used as an antibacterial drug candidate for multi-drug resistant *Staphylococcus aureus*, and further preclinical studies will be conducted.

What is claimed is:

1. A compound having the following formula (I):

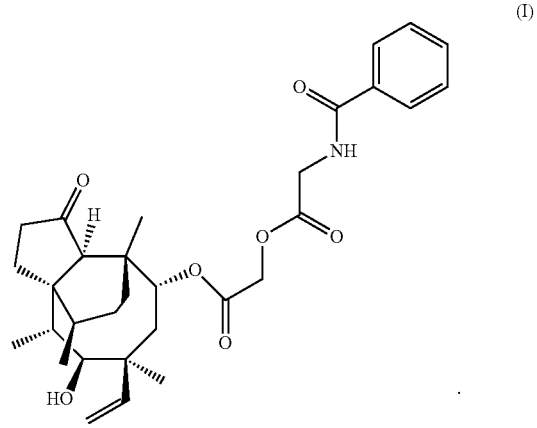 [SMILES: C=C[C@]1(C)C[C@@H](OC(=O)COC(=O)CNC(=O)c2ccccc2)[C@]2(C)CC[C@@H](C)[C@@]3(CCC(=O)[C@@H]23)[C@@H](C)[C@@H]1O]

(I)

2. A method of preparing the compound of formula (I) of claim 1, comprising: reacting a compound of formula (II) with a compound of formula (III) to obtain the compound of formula (I):

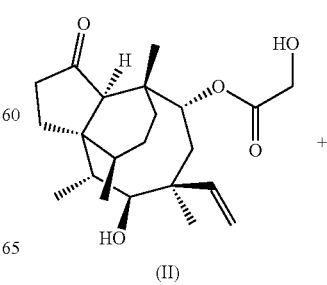

(II)

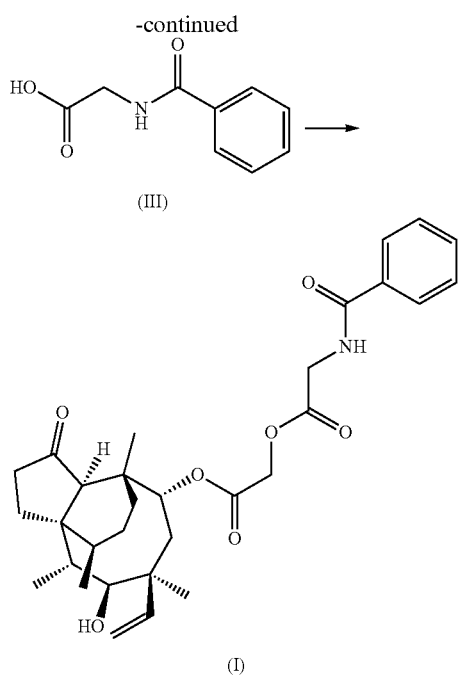

3. The method of claim 2, wherein the reaction of the compound of formula (II) with the compound of formula (III) comprises the following steps:
placing the compound of formula (II) and the compound of formula (III), in a molar ratio of 1:1 to 1:1.3, in a reactor;
adding an organic solvent and a catalytic amount of 4-dimethylaminopyridine (4-DMAP) under nitrogen atmosphere to obtain a reaction mixture;
stirring the reaction mixture at 0° C. for five minutes and then adding N,N'-dicyclohexylcarbodiimide (DCC) to the reaction mixture;
reacting the reaction mixture at 25-70° C. for 3 to 7 hours;
concentrating the reaction mixture and extracting with ethyl acetate to obtain a crude product; and
purifying the crude product on a silica gel fresh chromatography column with petroleum ether and ethyl acetate with a ratio of 1:1 to 4:1 as an eluent to obtain the compound of formula (I).

4. The method of claim 3, the organic solvent is toluene, 1,2-dichloroethane, or dimethylformamide (DMF).

5. The method of claim 4, wherein the organic solvent is 1,2-dichloroethane.

6. The method of claim 3, wherein the molar ratio of the compound of formula (II) and the compound of formula (III) is 1:1.1.

7. The method of claim 3, wherein the reaction mixture is heated at 60° C.

8. The method of claim 3, wherein the reaction mixture is reacted for 5 hours.

9. The method of claim 3, wherein the eluent is petroleum ether:ethyl acetate=3:1.

10. The method of claim 2, wherein the reaction of the compound of formula (II) with the compound of formula (III) comprises the following steps:
placing the compound of formula (II), a catalyst, and an ionic liquid in a reactor under nitrogen atmosphere, the catalyst being 12-molybdosilicic acid hydrate ($H_6Mo_{12}O_{41}Si$);
adding the compound of formula (III) to the reactor to form a reaction mixture;
heating the reaction mixture at 20-60° C. for 4-8 hours;
placing the reaction mixture in a separating funnel to separate a crude product;
purifying the crude product by recrystallization in methanol to obtain the compound of formula (I); and
recycling the ionic liquid.

11. The method of claim 10, wherein the ionic liquid is 1-octyl-3-methylimidazolium hexafluorophosphate ($C_{12}H_{23}F_6N_2P$),1-hexyl-3-methylimidazolium tetrafluoroborate or 1-butyl-3-methylimidazolium tetrafluoroborate.

12. The method of claim 11, wherein the ionic liquid is the ionic liquid is 1-octyl-3-methylimidazolium hexafluorophosphate.

13. The method of claim 10, wherein the compound of formula (II) and the compound (III) have a molar ratio of 1:1 to 1:1.3.

14. The method of claim 13, wherein the molar ratio of the compound of formula (II) and the compound of formula (III) is 1:1.1.

15. The method of claim 10, wherein the reaction mixture is heated at 30° C.

16. The method of claim 10, wherein the reaction mixture is heated for 6 hours.

* * * * *